United States Patent
Pasquino et al.

(10) Patent No.: US 11,660,375 B2
(45) Date of Patent: May 30, 2023

(54) PRODUCT AND METHOD FOR THE TREATMENT OF BIOPROSTHETIC TISSUES

(71) Applicant: Epygon, Paris (FR)

(72) Inventors: Enrico Pasquino, Savigny (CH); Marcio Scorsin, Luxembourg (LU)

(73) Assignee: Epygon, Paris (FR)

( * ) Notice: Subject to any disclaimer, the term of this patent is extended or adjusted under 35 U.S.C. 154(b) by 744 days.

(21) Appl. No.: 16/487,117

(22) PCT Filed: Nov. 30, 2017

(86) PCT No.: PCT/EP2017/080977
§ 371 (c)(1),
(2) Date: Aug. 20, 2019

(87) PCT Pub. No.: WO2018/153525
PCT Pub. Date: Aug. 30, 2018

(65) Prior Publication Data
US 2021/0213169 A1  Jul. 15, 2021

(30) Foreign Application Priority Data

Feb. 22, 2017  (EP) .................................... 17157490

(51) Int. Cl.
*A61L 27/36* (2006.01)
(52) U.S. Cl.
CPC ....... *A61L 27/3687* (2013.01); *A61L 2400/02* (2013.01); *A61L 2430/20* (2013.01)
(58) Field of Classification Search
None
See application file for complete search history.

(56) References Cited

U.S. PATENT DOCUMENTS 5,931,969 A     8/1999  Carpentier et al.
2002/0137024 A1  9/2002  Cunanan et al.

OTHER PUBLICATIONS

International Search Report of PCT/EP2017/080977 dated Mar. 23, 2018.
Written Opinion of PCT/EP2017/080977 dated Mar. 23, 2018.
Chang, H. W., Kim, S. H., Kim, K. H., & Kim, Y. J. (2011). Combined anti-calcification treatment of bovine pericardium with amino compounds and solvents. Interactive cardiovascular and thoracic surgery, 12(6), 903-907.
Coisne, C., Tilloy, S., Monflier, E., Wils, D., Fenart, L., & Gosselet, F. (2016). Cyclodextrins as emerging therapeutic tools in the treatment of cholesterol-associated vascular and neurodegenerative diseases. Molecules, 21(12), 1748.
Connolly, J. M., Alferiev, I., Kronsteiner, A., Lu, Z., & Levy, R. J. (2004). Ethanol inhibition of porcine bioprosthetic heart valve cusp calcification is enhanced by reduction with sodium borohydride. Journal of Heart Valve Disease, 13(3), 487-493.
Del Valle, E. M. (2004). Cyclodextrins and their uses: a review. Process biochemistry, 39(9), 1033-1046.
Friday, K. E., & Howard, G. A. (1991). Ethanol inhibits human bone cell proliferation and function in vitro. Metabolism, 40(6), 562-565.
Gidwani, B., & Vyas, A. (2015). A comprehensive review on cyclodextrin-based carriers for delivery of chemotherapeutic cytotoxic anticancer drugs. BioMed research international, 2015.
Jain, A. S., Date, A. A., Pissurlenkar, R. R., Coutinho, E. C., & Nagarsenker, M. S. (2011). Sulfobutyl ether 7 β-cyclodextrin (SBE 7 β-CD) carbamazepine complex: preparation, characterization, molecular modeling, and evaluation of in vivo anti-epileptic activity. AAPS PharmSciTech, 12(4), 1163-1175.
Jorge-Herrero, E., Fernandez, P., Escudero, C., Garcia-Paez, J. M., & Castillo-Olivares, J. L. (1996). Calcification of pericardial tissue pretreated with different amino acids. Biomaterials, 17(6), 571-575.
Kim, K. C., Kim, S. H., & Kim, Y. J. (2011). Detoxification of Glutaraldehyde Treated Porcine Pericardium Using L-arginine & NABH4. The Korean journal of thoracic and cardiovascular surgery, 44(2), 99.
Konakci KZ, Bohle B, Blumer R, Hoetzenecker W, Roth G, Moser B, Boltz-Nitulescu G, Gorlitzer M, Klepetko W, Wolner E, Ankersmit HJ. Alpha-GAL on bioprostheses: xenograft immune response in cardiac surgery. Eur J Clin Invest 2005;35: 17-23.
Manji, R. A., Zhu, L. F., Nijjar, N. K., Rayner, D. C., Korbutt, G. S., Churchill, T. A., . . . & Ross, D. B. (2006). Clinical Perspective. Circulation, 114(4), 318-327.
Patwardhan, A. M., & Vaideeswar, P. (2004). Stress strain characteristics of glutaraldehyde treated porcine aortic valve tissue following ethanol treatment. Indian Journal of Thoracic and Cardiovascular Surgery, 20(2), 67-71.
Ramp, W. K., & Demaree, D. N. (1984). Inhibition of net calcium efflux from bone by ethanol in vitro. American Journal of Physiology—Cell Physiology, 246(1), C30-C36.).
Rubin, E., & Rottenberg, H. (Jun. 1982). Ethanol-induced injury and adaptation in biological membranes. In Federation proceedings (vol. 41, No. 8, pp. 2465-2471).
Sardeto, E., Costa, F., Costa, I., Roderjan, J., Discher, E., Schneider, R., . . . & Lopes, S. (2006). Efficacy of AlCl3 and ethanol in the prevention of calcification of fragments of porcine aortic wall fixed in GDA. Brazilian Journal of Cardiovascular Surgery, 21(4), 409-417.
Schoen, F. J., & Levy, R. J. (2005). Calcification of tissue heart valve substitutes: progress toward understanding and prevention. The Annals of thoracic surgery, 79(3), 1072-1080.
Shen, Ming, et al. "Effect of ethanol and ether in the prevention of calcification of bioprostheses." The Annals of thoracic surgery 71.5 (2001): S413-S416.
Tung, M. S., & O'Farrell, T. J. (1993). The effect of ethanol on the solubility of dicalcium phosphate dihydrate in the system Ca (OH) 2—H3P04—H2O at 37° C. Journal of Molecular Liquids, 56, 237-243.
Vyavahare, N. R., Hirsch, D., Lerner, E., Baskin, J. Z., Zand, R., Schoen, F. J., & Levy, R. J. (1998). Prevention of calcification of glutaraldehyde-crosslinked porcine aortic cusps by ethanol preincubation: Mechanistic studies of protein structure and water-biomaterial relationships. Journal of Biomedical.
Vyavahare, N. R., Jones, P. L., Hirsch, D., Schoen, F. J., & Levy, R. J. (2000). Prevention of glutaraldehyde-fixed bioprosthetic heart valve calcification by alcohol pretreatment: further mechanistic studies. The Journal of heart valve disease, 9(4), 561-566.
Vyavahare, N., Hirsch, D., Lerner, E., Baskin, J. Z., Schoen, F. J., Bianco, R., . . . & Levy, R. J. (1997). Prevention of bioprosthetic heart valve calcification by ethanol preincubation: efficacy and mechanisms. Circulation, 95(2), 479-488.

*Primary Examiner* — Allison M Fox
(74) *Attorney, Agent, or Firm* — Finch & Maloney PLLC

(57) ABSTRACT

The invention concerns the treatment of bioprosthetic tissues a Cyclodextrin, preferably in association with Ethanol.

11 Claims, 10 Drawing Sheets

FIG. 4

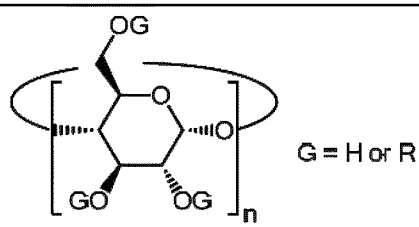

G = H or R

| Abbreviation | n | Substituent (R) | Number of R Group by CD |
|---|---|---|---|
| α-CD | 6 | (—) | 0 |
| β-CD | 7 | (—) | 0 |
| γ-CD | 8 | (—) | 0 |
| HPαCD | 6 | -CH$_2$-CHOH-CH$_3$ | 3.6 |
| RAMEα | 6 | -CH$_3$ | 10.8 |
| HPβCD | 7 | -CH$_2$-CHOH-CH$_3$ | 5.6 |
| KLEPTOSE® CRYSMEB | 7 | -CH$_3$ | 4 |
| Methyl-β-CD | 7 | -CH$_3$ | 1.6 |
| RAMEβ | 7 | -CH$_3$ | 12.6 |
| SBE7-β-CD | 7 | -(CH$_2$)$_4$-SO$_3$Na | 7 |
| TRIMETHYL-β-CD | 7 | -CH$_3$ | 21 |
| HPγCD | 8 | -CH$_2$-CHOH-CH$_3$ | 4.8 |
| RAMEγ | 8 | -CH$_3$ | 14.4 |

α-CD, α-cyclodextrin; β-CD, β-cyclodextrin; CD, cyclodextrin; CRYSMEB, crystalline methylated-β-cyclodextrin; γ-CD, γ-cyclodextrin; HPαCD, 2-hydroxypropyl-α-cyclodextrin; HPβCD, 2-hydroxypropyl-β-cyclodextrin; HPγCD, 2-hydroxypropyl-γ-cyclodextrin; Methyl-β-CD, methyl-β-cyclodextrin ; RAMEα, randomly-methylated-α-cyclodextrin; RAMEβ, randomly-methylated-β-cyclodextrin; RAMEγ, randomly-methylated-γ-cyclodextrin; SBE7-β-CD, sulfobutylether-7-β-cyclodextrin; TRIMETHYL-β-CD, TRIMETHYL-β-cyclodextrin.

PRODUCT AND METHOD FOR THE TREATMENT OF BIOPROSTHETIC TISSUES

CROSS REFERENCE TO RELATED APPLICATIONS

The present application is a United States national stage application of International patent application PCT/EP2017/080977 filed on Nov. 30, 2017 designating the United States, and claims foreign priority to European patent application EP17157490.8 filed on Feb. 22, 2017, the contents of both documents being herewith incorporated by reference in their entirety.

FIELD OF INVENTION

The present invention relates to the treatment of bioprosthetic tissues, in particular of biological tissues that are used in cardiovascular bioprostheses.

STATE OF THE ART

Calcification is one of the major causes of the failure of bioprosthetic heart valves derived from Glutaraldehyde-pretreated bovine pericardium or porcine aortic valves.1-3. Such pre-treatment are disclosed for instance in U.S. Pat. No. 5,931,969 (Baxter). The mechanism of this type of pathologic calcification is incompletely understood. In animal models, it has been shown that initial calcium nucleation sites are cell membranes, the nucleus, and intracellular organelles, such as the mitochondria of devitalized cells. With increasing duration of implantation, cell-associated calcific deposits increase in size and number. Direct collagen calcification in cusps and elastin calcification in the aortic wall subsequently occur. Various host factors, such as the young age of a recipient, and implant factors, such as Glutaraldehyde fixation, also aggravate calcification events.

Biological tissues are currently largely used for manufacturing bioprostheses, mainly in cardiovascular field, for long-term implants. Typically the biological tissues used for cardiovascular bioprostheses are represented by xenografts (e.g. native valves, pericardial sacs, blood vessels, tendons, etc. . . . ) mainly originated from bovine or porcine tissues. These biological tissues, before to be used for manufacturing bioprostheses and thereafter implanted must be chemically treated in order to avoid or to mitigate any foreign body or immunologic tissue response.

Typically in this field of research the biological tissues are chemically stabilized by means of a chemical reaction called "cross-link" aimed at bonding the collagen and elastin fibers together and stabilizing the extracellular matrix. The cross-link treatment has also the advantage to increase the mechanical properties of the tissues in order to grant its necessary long-term durability. This last aspect is of particular interest for the pericardial tissues or for the cusps of native animal valves used to assemble heart valve bioprostheses replacing the aortic, mitral, tricuspid or pulmonary diseased human valves.

The cross-link chemical reaction has been matter of many studies since in the last 50 years. Several methods using different molecules have been applied but the one nowadays still in use and largely applied by the heart valve manufacturer is the Glutaraldehyde.

However, Glutaraldehyde cross-link or fixation reaction promotes dystrophic calcification because of the chemical process between free aldehyde groups of Glutaraldehyde, phospholipids, fatty acids and cholesterol and residual antigenicity of the biological tissues[1,2,3]. Considerable efforts over many years through basic research have been directed toward developing a tissue treatment process to prevent calcification in Glutaraldehyde-fixed xenograft tissue. The main anticalcification strategies are aimed to extract lipids[4] or to neutralize toxic aldehyde residuals[5]. Glutaraldehyde-fixed xenografts have cellular/humoral rejection and calcify secondarily[3]. Tissue valve calcification is also initiated primarily within residual cells that have been devitalized[1].

Cyclodextrins

Structural Aspects of Cyclodextrins

The Cyclodextrins are cyclic natural oligosaccharides constituted by 6, 7 or 8 monomers of D-(+) Glucopyranose joined together with a $\alpha$,1-4 glucosidal bond and closed resulting in a conical-toroidal shape (FIG. 1). The three most common forms are $\alpha$-CD (6 units), $\beta$-CD (7 units) and $\gamma$-CD (8 units).

These macromolecules, thanks to the formation of intramolecular hydrogen bonds, assume a toroidal type tridimensional rigid structure, with an external surface containing $CH_2OH$ groups and an internal cavity with hydrophobic characteristics. This last one has dimensions, which depend from the number of units constituting the Cyclodextrin[6].

The presence of the cavity together with the solubility in water, deriving from the hydrophilic alcoholic functionalities, confers to Cyclodextrins the ability of complexation in aqueous solutions.

At room temperature the Cyclodextrins have the aspect of a crystalline white powder, odorless with a gentle sweet flavor.

The tridimensional structure constrains the hydroxyl groups on the external borders, whilst in the cavity are only present hydrogen and oxygen bonds. This condition creates a hydrophobic characteristic of the central cavity while the external surface is hydrophilic. In this way the Cyclodextrins acquire the possibility to host hydrophobic molecules inside the cavity and to be, at the same time, soluble in water. On the contrary the hydroxyl groups present on the external surface are able to link with aldehyde groups eventually present in the solution.

This explains the ability of Cyclodextrins to increase the water solubility of hydrophobic substances. When a molecule of opportune polarity and dimension is hosted into the inner Cyclodextrin cavity is created a supramolecular inclusion complex. The pushing force generating the inclusion involves various contributions such as steric fitting, hydrophobic effects, van der Waals interactions, electrostatic interactions and hydrogen link. The substances hosted into the Cyclodextrins' cavity are called "guest", while the Cyclodextrins are called "host".

The second advantage of inclusion complex formation consists in greatly modifying the properties of the molecule of interest (more precisely "drugs" in our case) in many ways such as improving drug stability, bioavailability, oral administration and drug interaction with biological membranes or cells. This latter advantage can easily explain the reason why Cyclodextrins have appealed so much attention and have been marketed worldwide in many industry areas from food, cosmetics, environmental engineering to chemical, pharmaceutical production and development.

Among the Cyclodextrins the most used is the $\beta$ family because the a family has a too small cavity while $\gamma$ family despite being very effective has very high manufacturing costs.

The $\beta$-Cyclodextrin (FIG. 3) can be used in pharmaceutical field thanks to their absence of toxicity when orally administered. In this field they are often used thanks to their host capacity to mask the distasteful flavor of some drugs, to covert liquid compounds in solid ones and furthermore to improve the bioavailability profile of many drugs especially thanks to the increased water solubility.

The natural β-Cyclodextrins can't be used for parenteral administration because they are nephrotoxic, however the hydroxypropyl derivatives (HP p-CD) of these Cyclodextrins (commercially known as Cavasol®) and the α-Cyclodextrins can be used for parenteral administration because they don't show any toxicity and allow the formulation of drugs totally insoluble in water (FIG. 2).

On the contrary the Methylated β-Cyclodextrin (M β-Cyclodextrin) are not suitable for parenteral administration even the somewhat lipophilic randomly M β-Cyclodextrin does not readily permeate lipophilic membranes, although it interacts more readily with membranes than the hydrophilic Cyclodextrin derivatives.

The Sulfobutyl Ether$_7$ β-Cyclodextrin (SBE$_7$ β-CD)[7] is another β-Cyclodextrin that has been more recently synthetized. SBE$_7$ β-CD is a highly water-soluble derivative of β-Cyclodextrin that is commercially available as Captisol®. The water solubility of SBE$_7$ β-CD (~70 g/100 ml at 25° C.) is significantly higher than the parent β-Cyclodextrin (1.85 g/100 ml at 25° C.). It has been already approved for parenteral use and thanks to its higher solubility could be even more effective than the HP β-CD. Therefore the SBE$_7$ β-Cyclodextrin could be a promising alternative to HP β-Cyclodextrin. Here below in FIG. 4 the structure of 3 isomeric structures of SBE$_7$ β-Cyclodextrin are represented.

The toxicity profile of the Cyclodextrins and derivatives has been extensively evaluated[9]. When administered orally, Cyclodextrins are generally considered safe as they do not cross the intestinal barrier, however, for the same Cyclodextrin the route of administration can modify its toxicity as demonstrated for native β-Cyclodextrin, which exhibits a limited toxicity after oral administration in animals as the acceptable daily intake has been limited to 5 mg/kg of body weight by the International Program on Chemical Safety (IPCS; WHO Food Additives Series 32), whereas parenteral or subcutaneous injections at higher doses get nephrotoxic affecting proximal tubules. The mode of clearance of Cyclodextrins from the organisms also depends on the route of administration. For example, HP β-Cyclodextrin is mainly eliminated by glomerular filtration in the kidneys and excreted into urine after intravenous injection in rats, whereas oral administration is mainly excreted through faeces in rats and dogs.

In summary all toxicity studies have demonstrated that orally administered Cyclodextrins are practically non-toxic, due to lack of absorption from the gastrointestinal tract. Furthermore, a number of safety evaluations have shown that γ-Cyclodextrin, 2-hydroxypropyl β-Cyclodextrin, Sulfobutyl Ether β-Cyclodextrin, Sulphated β-Cyclodextrin and Maltosyl β-Cyclodextrin appear to be safe even when administered parenterally[8].

Mode of Action of Cyclodextrins

In the pharmaceutical field, novel Cyclodextrin-based technologies of commercial interest are constantly being developed favoring the biological performances of the Cyclodextrins mostly in regards to drug delivery, biological safety and therapeutic efficiency[9]. These novel Cyclodextrins are mainly derived from native β-Cyclodextrin and their properties mainly depend on their degree of substitution (FIG. 5). These involve the methylated β-Cyclodextrin derivatives such as the randomly methylated β-Cyclodextrins (RAMEβ and KLEPTOSE® CRYSMEβ displaying 12.6 and four methyl groups, respectively), the HP-β-Cyclodextrin with hydroxypropyl groups randomly substituted onto the β-Cyclodextrin molecule, and also the sulfobutylether-7-β-Cyclodextrin (SBE7-β-Cyclodextrin) that are currently evaluated for the treatment of neurodegenerative disorders and atherosclerosis. Additionally, γ-Cyclodextrins have proven to be very useful in therapy, as they have not shown any hypersensitivity reaction, unlike Sugammadex. This modified Cyclodextrin used in anesthesia to reverse the effect of neurovascular blocking drugs has been involved in allergic response in some patients. As therapeutic agents, the mode of action of Cyclodextrins and their derivatives can occur in two ways. The first one implies the direct biological action of the Cyclodextrins on cell membranes whereas the second one is rather indirect using the encapsulation potentiality of Cyclodextrins as drug carriers.

The direct action of the Cyclodextrins on cells consists in extracting lipids (cholesterol and phospholipids) as well as some proteins from cell membranes modifying the molecular composition of the lipid bilayers and thus their properties (FIG. 5). It has been described that α-Cyclodextrin removes phospholipids, β-Cyclodextrin extracts phospholipids and cholesterol whereas γ-Cyclodextrin is less lipid-selective than other Cyclodextrins.

In the second one the Cyclodextrins are widely used as drug delivery carrier via nasal mucosae, pulmonary-, ocular-, dermal-, intestinal- and brain-barriers as these molecules improve delivery and bioavailability of hydrophilic, hydrophobic as well as lipophilic drugs.

Cyclodextrins have also been extensively used to improve biocompatibility and enhanced bioavailability, when incorporated into complexes with active drug compounds, thus enhancing drug efficacy. The combination of Cyclodextrins and drug compounds into complexes has been applied in researches for the treatment of atherosclerosis and neurodegenerative diseases such as Alzheimer's and Parkinson's diseases. In addition, Cyclodextrins can be used as a carrier enabling the selective binding to biomolecules of interest, as reported for example, for cholesterol crystal detection in atherosclerosis.

Therefore, the direct action mode of Cyclodextrins has proven effects on cells, promoting an effective extraction of cholesterol and phospholipids from the lipids raft of cell membranes. The indirect action mode highlights the complexation capacity of Cyclodextrins allowing an even more effective removal of lipids and aldehyde groups.

Ethanol

Ethanol has been used, since several years for the treatment of bioprosthetic tissues, such as aortic prosthetic cusps, bovine or porcine pericardial tissue, with the aim to mitigate the process of dystrophic calcification when implanted at long-term.

The Ethanol has been applied in treatments alone or associated with other substances in general after a cross-link treatment obtained with Glutaraldehyde.

In the following a scientific review about the different bioprosthetic tissue treatments based on Ethanol (alone or combined with other molecules) is presented. The possible mechanism of action and efficacy of Ethanol, as anticalcification method, have been analyzed.

The 80.0% Ethanol pretreatment of Glutaraldehyde-crosslinked cusps extracted almost all cholesterol and phospholipids from the cusp samples[10]. It has been hypothesized that phospholipids present in devitalized cells of bioprostheses are an initial source of phosphorus in heart valve calcification due to phosphorester hydrolysis. Other studies also have looked at the connection between cholesterol and calcification in atherosclerotic plaques. It has been shown that cholesterol levels increase progressively with age, correlating directly with the risk of coronary artery disease. Cholesterol also alters calcium transit across cell membranes, cystolic calcium levels, and membrane fluidity in arterial smooth muscle cells. The mechanism by which cholesterol content of the cell membrane correlates with intracellular calcification remains incompletely understood.

These data strongly suggest that the changes brought about by Ethanol pretreatment in collagen conformation are stable and may be important in explaining the anticalcification mechanism. Such a conformational change may be responsible for the observed reduced cuspal adsorption of lipids or proteins due to ethanol pretreatment. This also warrants for further research on protein-protein and protein-lipid interactions with respect to collagen and their roles in bioprosthetic heart valve calcification[10].

The cuspal collagen conformational changes induced by Ethanol treatment were persistent. In addition, there was resistance to digestion by collagenase. Therefore it may be hypothesized that anticalcification effect and collagen conformational change brought about by Ethanol pretreatment could result in a more durable bioprosthesis[10].

The Ethanol pre-incubation of glutaraldehyde-cross-linked porcine aortic valve bioprostheses is a highly efficacious pre-treatment for preventing calcification of porcine aortic valve cusps in both 60-day rat subdermal implants and sheep mitral valve replacements (150 days). Ethanol was chosen as an anticalcification agent due to its known interference in the cellular metabolism of calcium in bone-line cells as well as in fibroblasts.[11,12] The presence of Ethanol has been shown to break down cellular membranes and disorder acyl chains of phospholipids that affect many cellular activities[13]. Furthermore, Ethanol has been shown to significantly inhibit calcium phosphate nucleation and phase transformations due to its interactions with water[14]. In a previous publication[15] concerning Ethanol inhibition of bioprosthetic heart valve cusp calcification, the 80.0% Ethanol pretreatment extracted almost all phospholipids and cholesterol from glutaraldehyde-cross-linked cusps.

To understand the mechanism of action of Ethanol in preventing bioprosthetic heart valves calcification, leaflet samples were analyzed for total lipid and cholesterol content before and after pretreatment.

Ethanol with concentration higher than 50.0% was a very efficient extractor of both cholesterol and phospholipids, with nearly complete extraction of both 15 as described in FIG. 6. Membrane-bound phospholipids are considered to be donors of phosphorous in the initial stages of mineralization of bioprosthetic heart valves because of hydrolysis by alkaline phosphatase. Complete removal of phospholipids, which are initial sites of calcification, may partially explain the mechanism of action of Ethanol. However, the results with chloroform-methanol (2:1) treatment demonstrated that this delipidation regimen resulted in the complete extraction of both total cholesterol and phospholipid (Table 1).

In the rat subdermal model the implant duration was extended to 60 days. The controls calcified severely (calcium level, 236±6.1 µg/mg tissue). The 80.0% Ethanol (pH 7.4 for 24 hours) pretreatment was most effective, with complete inhibition of calcification with the calcium levels comparable to unimplanted bioprosthetic tissue (calcium level, 1.87±0.29 µg/mg tissue), whereas the 60.0% Ethanol pretreatment was partially effective (calcium level, 28.5±12.0 µg/mg tissue). Therefore, the 80.0% Ethanol pretreatment was found to be the best condition for preventing leaflet calcification in both the 21- and 60-day rat subdermal models.

Porcine aortic valve bioprostheses treated with Ethanol and implanted in sheep model for 150 days showed a significant reduction in leaflet calcium accumulation in respect to the control (Glutaraldehyde fixed leaflets) as described in Table 2.

TABLE 1

| Group | Cholesterol | Phospholipids |
| --- | --- | --- |
| Control | 13.3 ± 0.4 | 17.2 ± 0.8 |
| 40% Ethanol | 13.9 ± 0.7 | 16.5 ± 1.5 |
| 60% Ethanol | 0.30 ± 0.05 | 4.93 ± 1.9 |
| 80% Ethanol | 0.14 ± 0.02 | 1.08 ± 0.1 |

Thus, these data indicate that although lipid extraction may play a part in the mechanism of action of Ethanol, lipid extraction alone cannot completely explain the anticalcification efficacy of Ethanol, and Methanol may be altering the other factors that influence mineralization Table 1.

TABLE 2

| Group | Ca |
| --- | --- |
| Control | 32.51 ± 11.46* |
| 80% Ethanol treatment | 5.22 ± 2.94* |
| Unimplanted | 2.80 ± 0.70 |

The stress strain characteristics of tissues treated with Ethanol were evaluated in aortic valve of porcine tissues cusps[16]. This study compares uniaxial stress strain properties of untreated porcine aortic cusps with those of the Glutaraldehyde treated cusp and those of the Ethanol incubation following Glutaraldehyde.

The untreated cusps provided the control (C) while the Glutaraldehyde treated cusps (G) and the Ethanol treated cusps following Glutaraldehyde fixation (G+A) represented the test samples.

There was significant difference between the groups (C), (G+A) for the parameter maximum load (p=0.002). For the parameter maximum stress, there was significant difference between the groups (G+A) and both groups (G) and (C), the p value being 0.047 and 0.007 respectively. The group (G+A) also showed increased ability to elongate on stress, (maximum displacement), as compared to both groups (G) and (C) {p=0.025 and p=0.049 respectively}. The group (G+A) also showed significantly higher maximum strain as compared to both groups (G) and (C) {p=0.006 and p=0.027 respectively.

The Ethanol treatment of Glutaraldehyde tanned tissue not only preserves the tensile strength, which is increased following Glutaraldehyde tanning, but also improves the extensibility in uniaxial testing in circumferential direction. This change in physical characteristics may help in preserving the durability of aortic cusps. The reduction in propensity to calcify and the ability of cuspal tissue to lengthen on stress might help in preventing structural dysfunction. However, it would be appropriate to consider long-term in-vivo durability studies of alcohol treated Glutaraldehyde tanned porcine aortic valves in-vivo to test this hypothesis.

In another study the anticalcification effect of Ethanol in relationship to Glutaraldehyde cross-link was evaluated. The authors state that low-molecular weight alcohols (Methanol, Ethanol and Isopropanol) were effective in calcium mitigation of porcine aortic valve cusps. The storage of tissues in Glutaraldehyde after Ethanol treatment allowed a partial return of calcification suggesting a role for Ethanol-Glutaraldehyde interaction in preventing the tissue calcification. However when the porcine cusps were stored in ethanolic Glutaraldehyde the anticalcification effect of Ethanol persisted[17].

In another study Carpentier, in 2001, studied the effect of Ethanol, Ether and surfactant treatments on pericardium samples pretreated with 0.6% Glutaraldehyde[18]. Ethanol, Ether, or the Tween 80 surfactant, and combinations thereof were used to carry out the lipid extraction. The treated tissues were implanted subcutaneously in 50 juvenile rats for 4 and 6 months. After 6 months of implantation, only in the groups of Ethanol with surfactant and Ether with surfactant the calcium level was significantly lower than in the control group. In previous studies was showed that Ethanol is quite effective in extraction of phospholipids and that they play an important role in the process of calcification[10]. On the contrary the analyses showed that Ethanol extraction does not completely eliminate triglycerides in bovine pericardium, whereas extraction by ether totally removed triglycerides. The calcium content of these two groups, however, was not significantly different after 6 months of implantation implying that the role of triglycerides in calcium deposition is non-significant. In conclusion, treatments by Ethanol or Ether alone or surfactant alone are less efficient than the combination of these treatments. The fact that the combination of treatments is more efficient than any of the single treatments tends to prove that the mechanism of extraction and the products extracted by each treatment are slightly different. As a practical conclusion of this work it could be said that in the currently used procedure of bioprosthetic valve preservation, it might be beneficial to increase the concentration of Ethanol or its length of incubation or to add Ether treatment to the surfactant treatment.

The most efficient pretreatments were the combination of Ethanol and surfactant (calcium content: 15.5±6.8 µg/mg dry tissue after 6 months implantation) or the combination of Ethanol, Ether, and surfactant (13.1±6.2 µg/mg dry tissue) when compared with surfactant alone (42.9±12.7 µg/mg dry tissue).

The anticalcification effect of Ethanol is well evident from a number of scientific publications. Despite the effectiveness of the Ethanol treatment on both porcine aortic cusps and pericardial tissue, some minor residual calcification were still present and suggested to the researchers the exploration of additional combined treatments in order to further mitigate the calcific dystrophic deposition in tissues.

Connoly[19] evaluated the post-treatment with sodium borohydride of Ethanol treated porcine aortic cusps. Ethanol pretreatment significantly inhibited calcification compared with controls (13.3+/−5.6 versus 119.2+/−6.6 Ca µg/mg tissue; p<0.001). However, sodium borohydride reduction under optimized conditions combined with Ethanol pretreatment optimally reduced calcification (1.16+/−0.1 Ca µg/mg; p<0.05), whereas levels after sodium cyanoborohydride treatment (23.6+/−10.4 Ca µg/mg) were not significantly different to those after Ethanol alone. Neither reducing agent was effective in inhibiting calcification without Ethanol pretreatment.

Some other authors[20] adopted Ethanol as phospholipids solvent together with aminoacids to detoxicate the pericardial tissue. Groups of bovine pericardium samples were fixed with 0.5% GA. Urazole and glutamate were used to neutralize the free aldehyde and some solvents (Ethanol with Octanol or Octanediol) to reduce the phospholipid content in the bovine pericardial tissue. Urazole and glutamate alone significantly decreased the $Ca^{2+}$ and inorganic phosphorus (IP) concentrations (without any anti-calcification treatment, $Ca^{2+}$: 277.85±17.51 µg/mg; IP: 147.07±8.32 µg/mg), but when used with organic solvents, the $Ca^{2+}$ and inorganic phosphorus concentrations were the lowest ($Ca^{2+}$: 0.05±0.04 µg/mg; IP: 3.36±0.61 µg/mg).

The purpose of the study published by Kim[21] was to evaluate the synchronized synergism of using L-arginine and sodium borohydride ($NaBH_4$), compared with Ethanol and L-lysine, in Glutaraldehyde treated porcine pericardium from the standpoint of calcification and tissue elasticity. Porcine pericardium was fixed at 0.625% Glutaraldehyde (7 days at room temperature after 2 days at 4° C.). An interim step of Ethanol (80%; 1 day at room temperature) or L-lysine (0.1 M; 2 days at 37° C.) or L-arginine (0.1 M; 2 days at 37° C.) was followed by completion of the Glutaraldehyde fixation. L-lysine and $NaBH_4$ pretreatment (183.8±42.6 µg/mg, p=0.804), and L-arginine and $NaBH_4$ pretreatment (163.3±27.5 µg/mg, p=0.621) did not significantly inhibit calcification compared to the control (175.5±45.3 µg/mg), but Ethanol and $NaBH_4$ pretreatment did (38.5±37.3 µg/mg, p=0.003). Finally $NaBH_4$ pretreatment seemed to decrease the calcification of porcine pericardium fixed with Glutaraldehyde, but only with Ethanol.

Another study[22] was enhanced in order to evaluate the efficiency of aluminum chloride in isolation or associated with Ethanol to prevent calcification and inflammatory reaction with fragments of porcine aortic wall fixed in Glutaraldehyde and subdermally implanted in young rats. Samples of porcine aortic wall were implanted in the subdermal tissue. The specimens were previously subjected to three different methods of treatment: I (glutaraldehyde), II (glutaraldehyde+aluminum), III (glutaraldehyde+ethanol+aluminum). Atomic absorbance spectroscopy showed similar calcium levels for both Groups II and III, but significantly less than in Group I. Treatment with aluminum chloride inhibits calcification of specimens of aortic wall after implantation and reduces inflammatory reaction. The combined use of Ethanol with aluminum chloride is more efficient to inhibit calcification and also to diminish inflammatory reaction.

The above discussed literature review clearly indicates that the Ethanol treatment of bioprosthetic tissues is normally highly effective in preventing the tissue dystrophic calcification after long-term implants in animal models. The tissue calcium content reduction versus control is always significant when the biomaterials are pretreated with Ethanol and cross-linked with Glutaraldehyde.

Ethanol is efficient in solubilizing and extracting the lipid raft (cholesterol and phospholipids) from the cell membranes identified as the major responsible for triggering calcification. The best efficiency in term of lipid extraction is obtained at concentrations of 80% but good tissue calcification reduction is already visible with concentrations of 50%[15].

The application of alternative tissue cross-link treatments (Triglycidylamine, Genipin, Neomicin) or post-treatments, such as Urazole, Glutamate, Dodium Borohydride, Aluminum Chloride or others, are further reducing the propensity to calcification only when associated to Ethanol.

BRIEF DESCRIPTION OF THE DRAWINGS

FIG. 4 shows different cyclodextrins and their characteristics.

DESCRIPTION OF THE INVENTION

Figure 1:
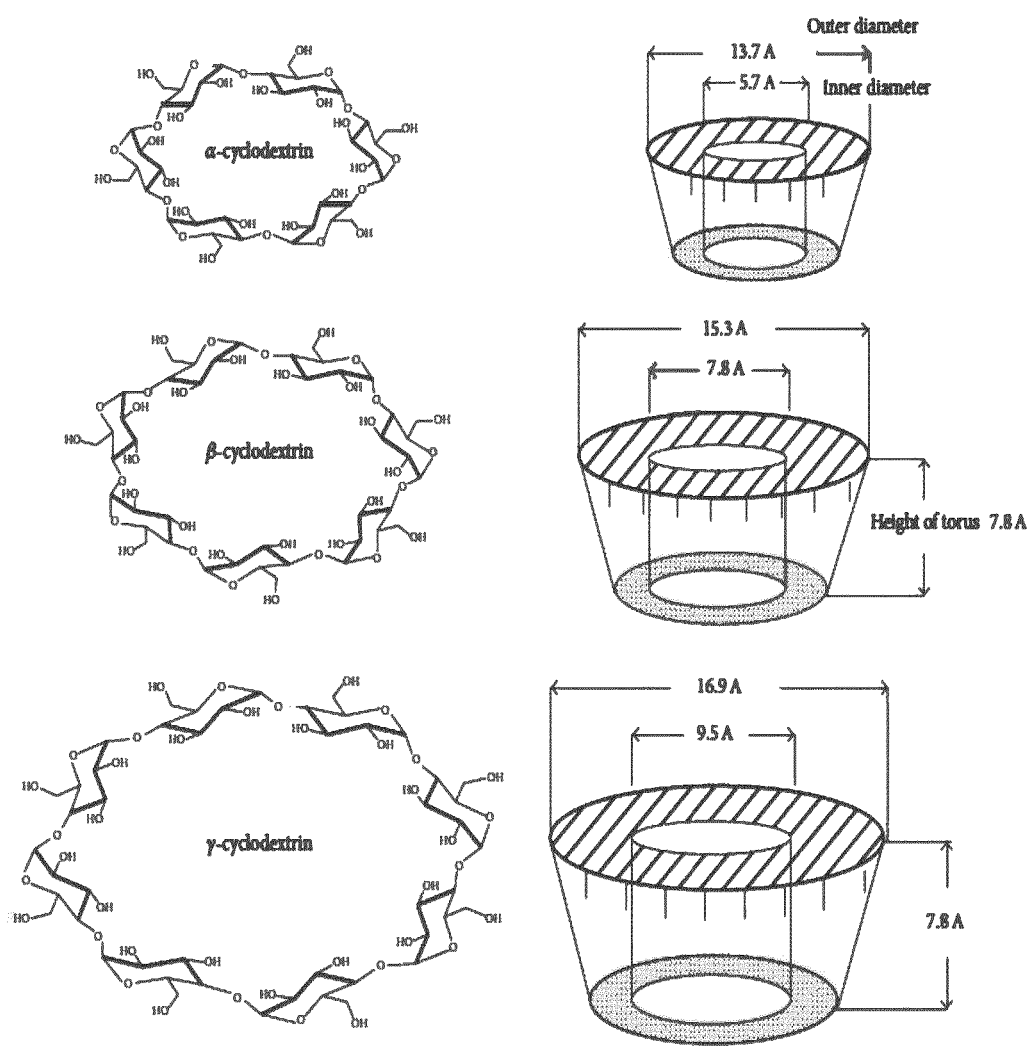
FIG. 1 shows schematically different cyclodextrins.
Figure 2:
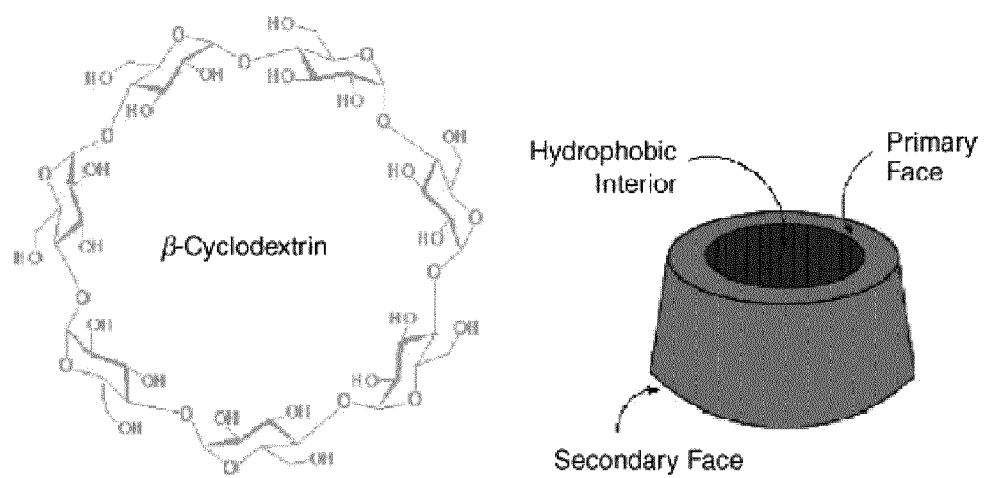
FIG. 2 shows schematically the structure of p-cyclodextrin.
Figure 3:
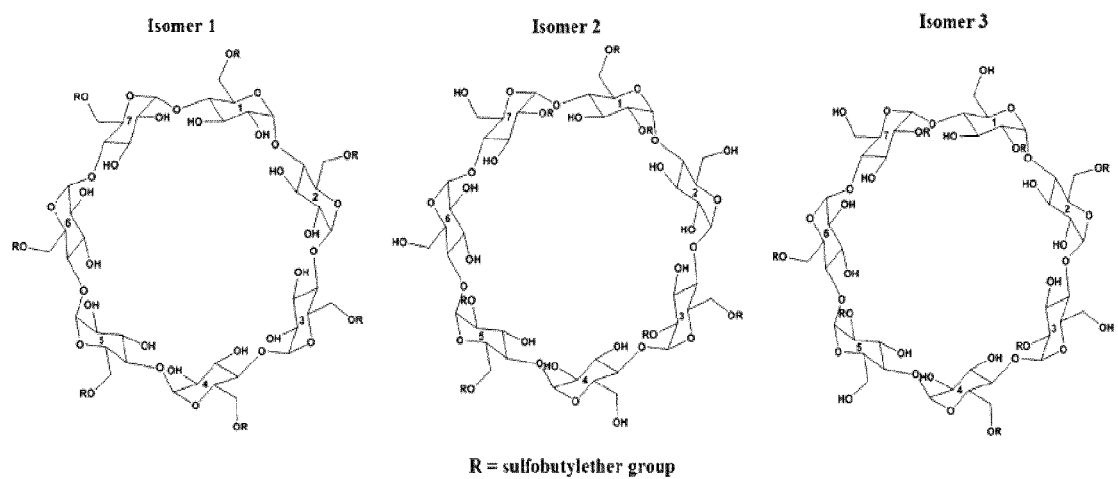
FIG. 3 shows different isomers of cyclodextrins.
Figure 5:
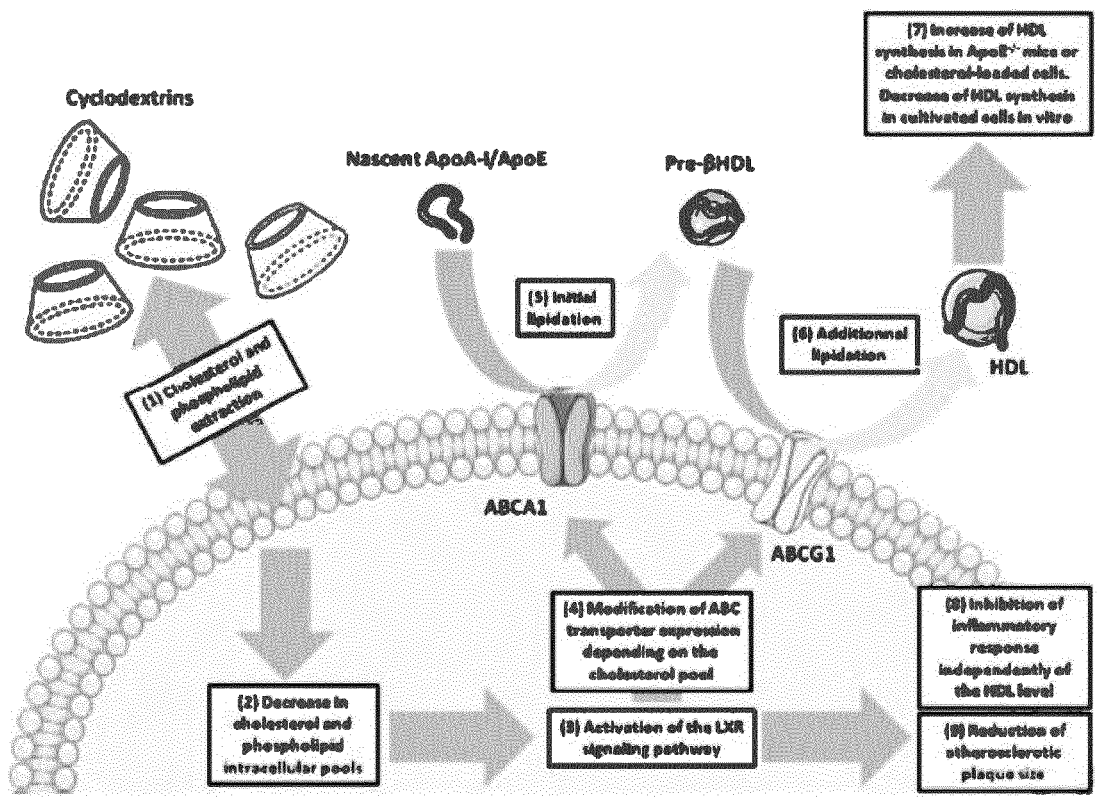
FIG. 5 shows a direct action of cyclodextrins on cells.
Figure 6:
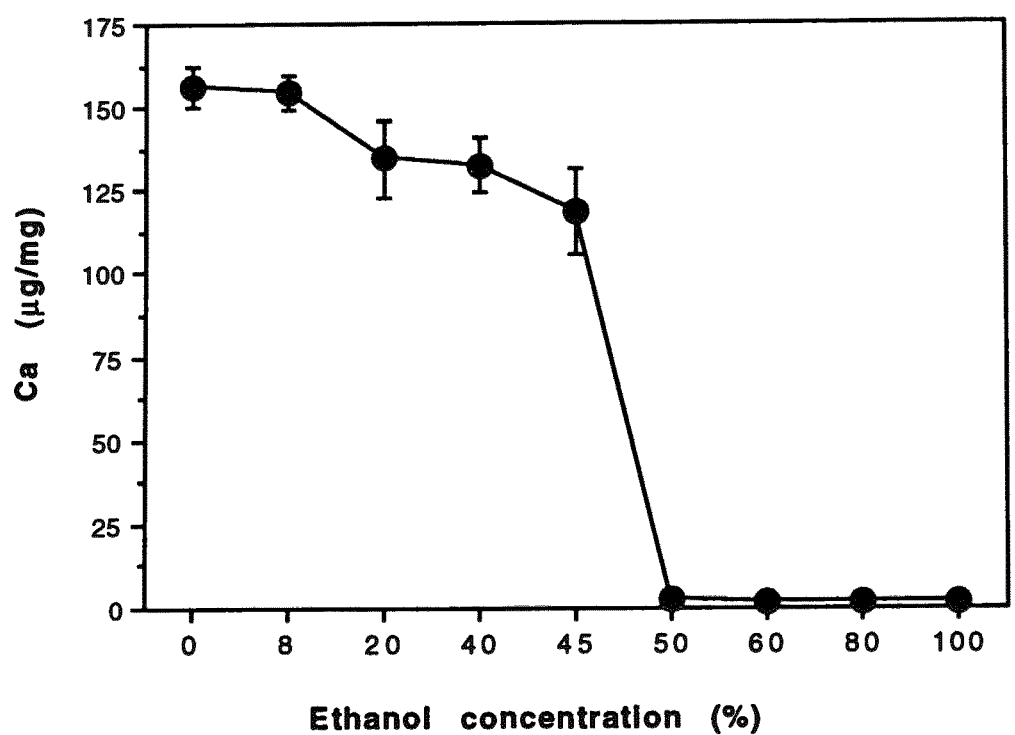
FIG. 6 shows the extraction of cholesterol/phospholipids as a function of ethanol content.

The present invention generally relates to a novel and original use of Cyclodextrin in the treatment of bioprosthetic tissues.

Using a Cyclodextrin in this treatment provides bioprosthetic tissues with a long-term mechanical and biological durability, after implant. Such properties are especially critical for heart valve bioprostheses.

Cyclodextrins belong to a large family of molecules but for the present invention the most accredited are those of the β family. The functionalized β-Cyclodextrins and in particular the HP β-Cyclodextrin and the SBE β-Cyclodextrins have been approved for parenteral use. They therefore are expressing all desired chemical action without any damages for the excretory organs even if they are present in traces.

Advantageously, the Cyclodextrin is used in combination with Ethanol.

The tissue treatment based on Ethanol in aqueous concentration, higher than 50%, has demonstrated to be highly effective in extracting the phospholipids. The Ethanol effectiveness is closely related to the Glutaraldehyde cross-linking of bioprosthetic tissues. The mechanism is unclear but the Ethanol treatment appears to be more effective when applied after a Glutaraldehyde based cross-linking process.

The Cyclodextrin action can be expressed as direct, with primary extraction of lipidic molecules, and indirect with complexation of the lipidic molecules already extracted. It is in this second action mode that Cyclodextrins can complex phospholipids already solubilized by Ethanol.

In general the action of Cyclodextrins, when applied to biologic tissues, can be explained as a steric interaction or a weak covalent bound between its hydrophobic cavity and the lipidic molecules. In other terms it is about a weak covalent bound of Cyclodextrins and lipidic molecules without occurring any chemical reaction.

The use of a specific derivative of Cyclodextrin for the treatment of biologic tissues is disclosed in patent application US2002/137024. This prior art teaches that sulfonated and sulfated polyanions are able to block the calcium nucleation sites in biologic tissues used for prosthetic devices. The mechanism of action of these chemicals is not described but one can unambiguously deduct from the teaching of this document that the sulfonated and/or sulfated functional groups are responsible for the blocking of the calcium nucleation sites. As a matter of fact, the examples reported in US2002/137024 refer to completely different molecules, having in common the sulfonate/sulfate groups only. A few examples of the polyanions mentioned in US2002/137024 are sulfated Cyclodextrins being just one of them. It is possible to infer that the sulfonate/sulfate groups are able to block the calcium nucleation sites, presumably because of the affinity between calcium and sulfate anions. In other words, a sort of competitive action of sulfate/sulfonate anions against the phosphate groups of the phospholipids, which are clearly identified in US2002/137024 as calcium nucleation sites despite already well known in the prior art.

In general, Cyclodextrins do not contain functional sulfonate or sulfate groups. It should be underlined that Cyclodextrins are usually neutral molecules and not ionic compounds. Sulfated Cyclodextrin is just one derivative of the large class of Cyclodextrins and the functionalization is aimed at obtaining a more soluble or tolerable molecules for i.v. injection. Therefore there is nothing in US2002/137024 suggesting the use of Cyclodextrin itself as blocking agents for calcium nucleation sites. In fact, US 2002/137024 is even teaching away the use of Cyclodextrin by itself as blocking agent for calcium nucleation sites.

In the present invention, the selected Cyclodextrin is acting in a completely different way in respect to what described in US2002/137024. The Cyclodextrin by itself is removing phospholipids from the tissue thanks to its hydrophobic cavity, which would sequestrate the phospholipid fat chains.

Ethanol and Cyclodextrin can be used simultaneously or separately, in any order.

The bioprosthetic tissues (native valve cusps, bovine or porcine pericardial tissues) are selected for absence of defects and thickness. The selected patches or cusps are submitted to a cross-link process aimed at stabilizing the collagen in order to avoid any immunologic or foreign body tissue response. The cross-link process can be conducted with different molecules, but typically Glutaraldehyde at a concentration ranging between 0.1% to 1% for a period of 12 h to 48 h or more is used.

Figure 7:
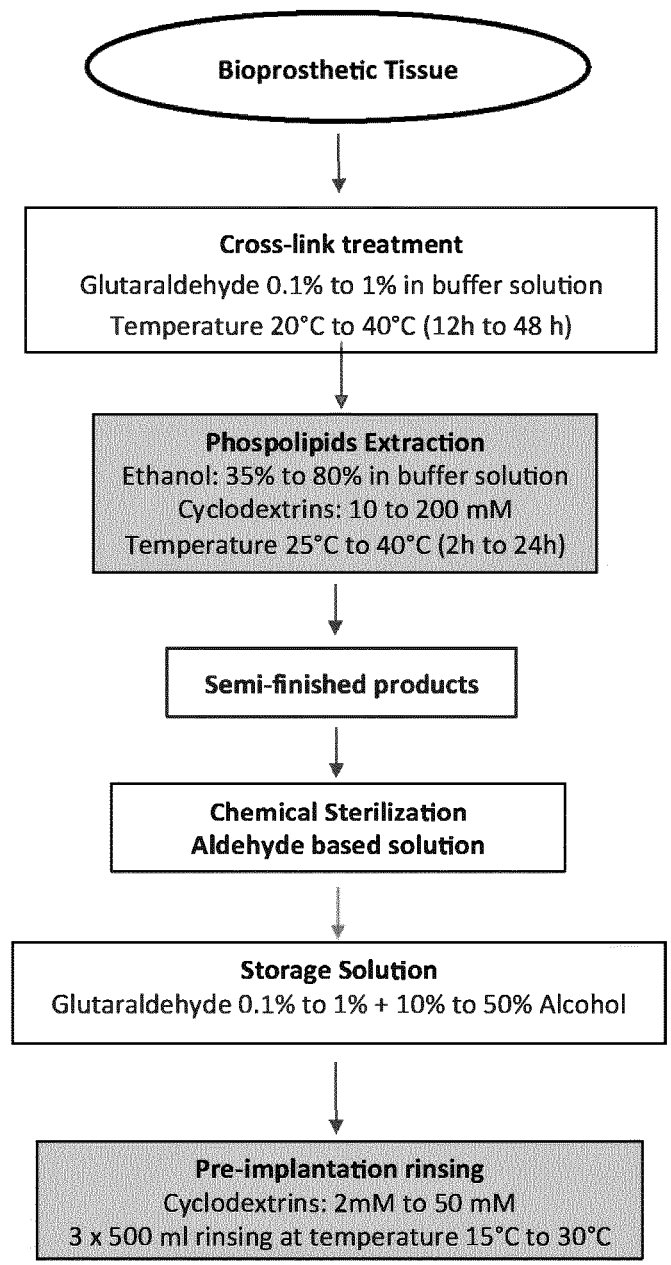
FIG. 7 shows a flow chart of a combined delipidation treatment.

Preferably, the combined delipidation treatment (FIG. 7) is performed combining Ethanol at a concentration between 35% and 80% solubilized in a buffered solution at PH 7.4 with 10 mM to 200 mM of β-Cyclodextrin for 2 h to 24 h at a temperature ranging between 25° C. and 40° C.

After the delipidation treatment the patches are assembled in semi-finished or finished assemblies and then chemically sterilized with an aldehyde based solution eventually added with short chain alcohol molecules.

Finished devices are then stored in a solution composed by aldehyde at concentration of 0.1% to 1% and eventually added with short chain alcohol molecules in concentration of 10% to 50%.

In order to add a tissue detoxification process, aimed at removing aldehyde free molecules from the bioprosthesis before the implant, a pre-implantation rinsing procedure is performed.

This pre-implantation rinsing is performed with three aliquots of 500 ml of a solution of p-Cyclodextrins at a concentration of 10 mM to 200 mM at a temperature of 15° C. to 30° C.

Figure 8:
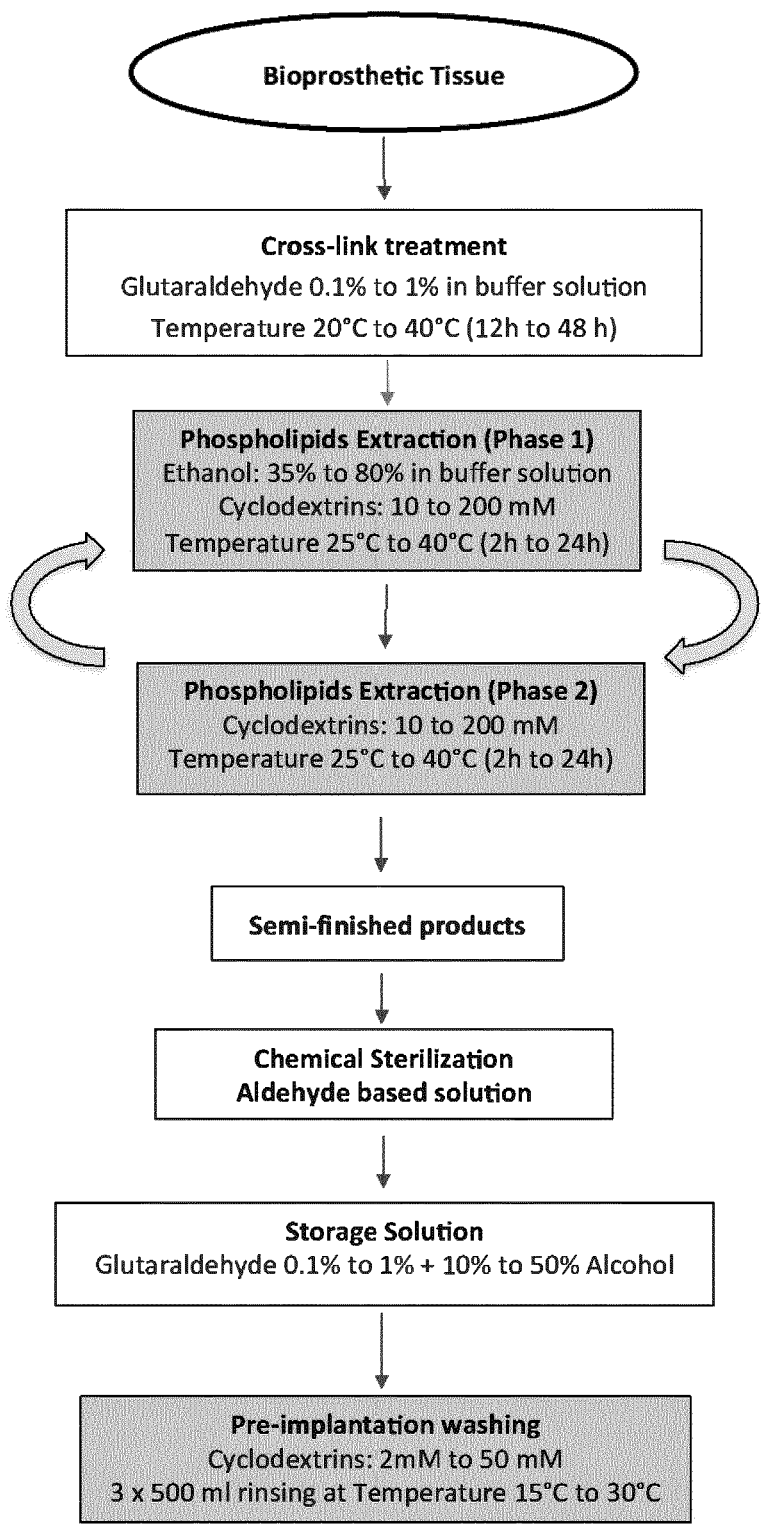
FIG. 8 shows a flowchart of a phospholipid extraction in two phases.

In another embodiment the phospholipid extraction can be performed, after the tissue cross-link, in a disjoined manner in two phases (FIG. 8). First the Ethanol treatment is performed followed by the β-Cyclodextrin. Both treatments performed at the same concentrations and conditions described in FIG. 7.

The phospholipid extraction, as described in FIG. 8, can be conducted in inverted way anticipating the exposition to β-Cyclodextrin followed by Ethanol treatment at the same concentrations and conditions.

Figure 9:
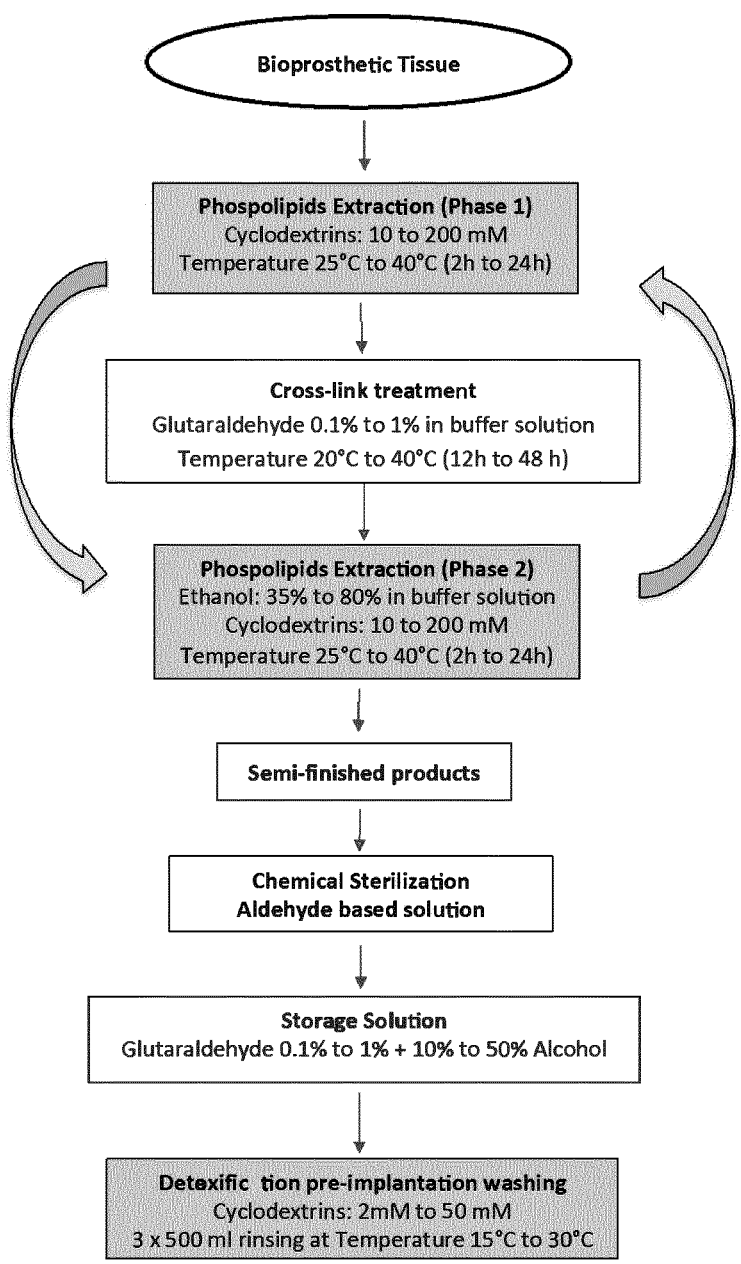
FIG. 9 shows a flowchart of an alternative phospholipid extraction in two phases.

The combined treatment of Ethanol and β-Cyclodextrin can be performed anticipating the p-Cyclodextrin treatment directly on the bioprosthetic tissue before the cross-link procedure (FIG. 9) followed by a treatment with an Ethanol solution. The concentration of Ethanol and β-Cyclodextrin can be the same as described in FIG. 7. This disjoined treatment can be applied in inverted order if needed.

The rationale for anticipating the β-Cyclodextrin treatment, before the cross-link procedure (FIG. 9), is based on the direct active mode of Cyclodextrins to directly delipidate the bioprosthetic tissues. This is the same active extraction capacity expressed by Cyclodextrins observed in experiments where these molecules were able to extract cholesterol and other lipids from the atherosclerotic plaques in arterial vessels (FDA approved a Cyclodextrins as orphan drug treatment in a rare pediatric disease where infants show abnormally high plasma concentration of cholesterol with atherosclerotic plaques at 2-3 years age).

Figure 10:
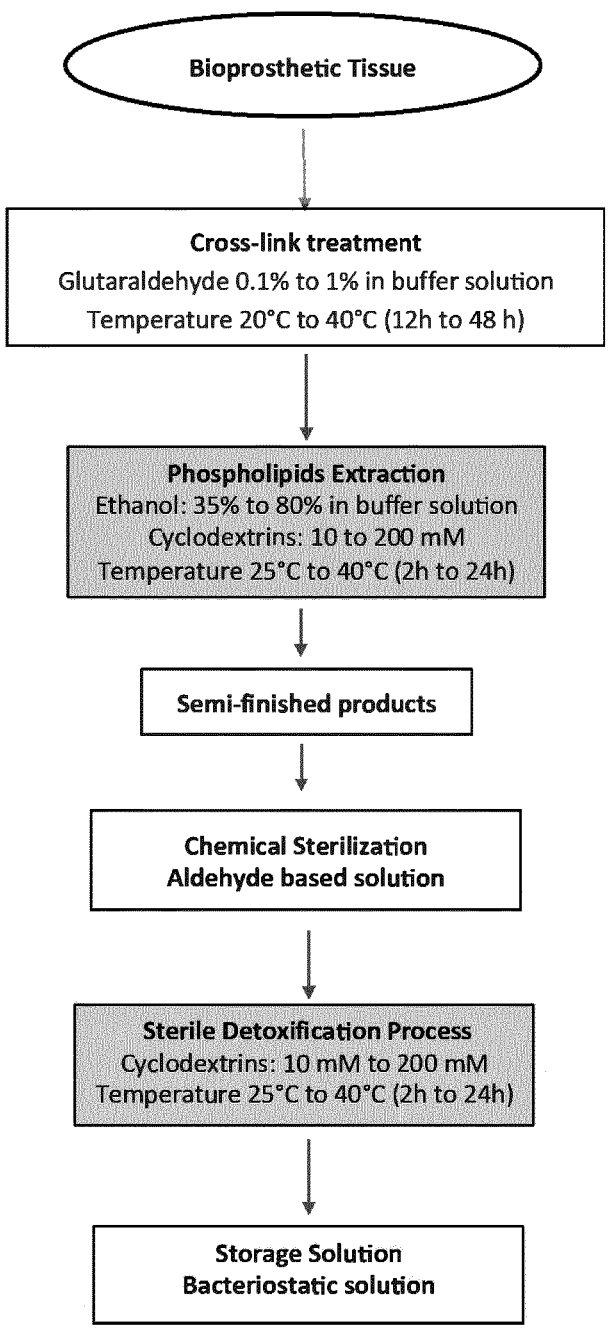
FIG. 10 shows a flowchart of a method including a further detoxification process.

In another embodiment after the phospholipids extraction as described in the previous treatments with Ethanol and Cyclodextrins the process could include a further detoxification process, based on Cyclodextrins, aimed at removing, in effective way, the residual aldehyde molecules (FIG. 10). The aim of this chemical treatment variation is required in order to store the bioprosthesis in a bacteriostatic aldehyde-free storage solution. As previously described it is quite important the removal of aldehydes from the storage solution since it has been demonstrated that storing the bioprosthesis in Glutaraldehyde could partially override the positive anticalcification effect given by the Ethanol treatment. This is the reason why in the previous embodiments the storage media, described in FIGS. 7 to 9 where based on Glutaraldehyde solution added with a certain amount of short-chain alcohols.

An important step forward in the bioprosthetic tissue treatment is represented by the tissue dehydration in association with a ethylene oxide sterilization. This is done in order to more easily store the bioprostheses avoiding chemical sterilization and their handling especially when they must be collapsed and used in transcatheter procedures.

Figure 11:
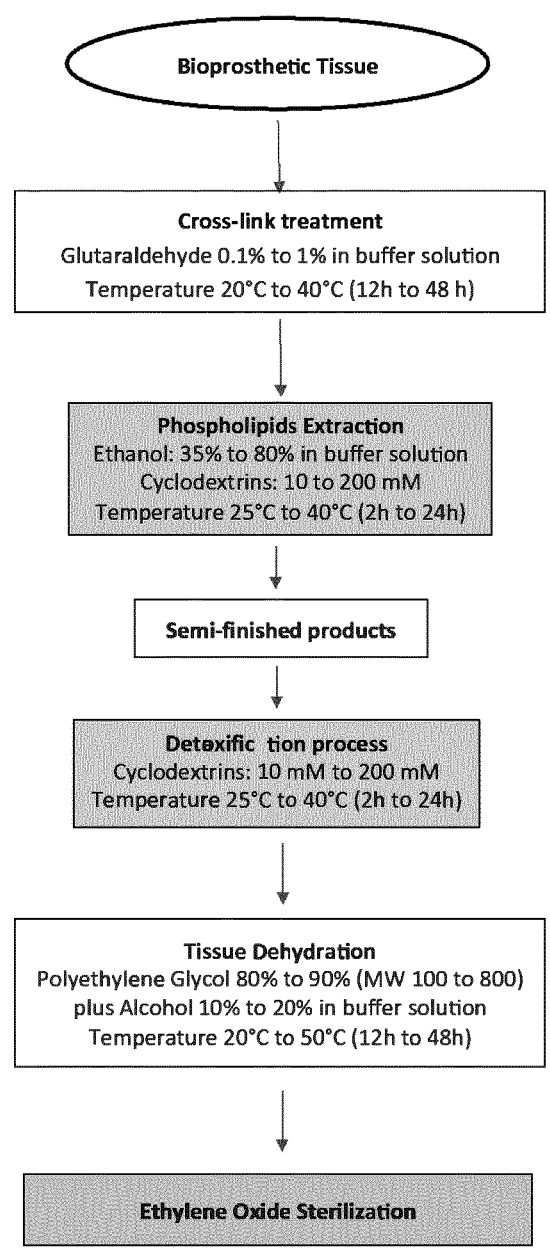
FIG. 11 shows a flowchart of a method including a tissue dehydration procedure.

The previous treatment embodiments previously presented, as possible variations, can be associated to the tissue dehydration procedure. As for example in FIG. 11, after the delipidation, a detoxification process is performed with β-Cyclodextrin is completed with the aim to remove aldehyde molecules from the tissue. When the detoxification is completed a tissue dehydration procedure can be started. This treatment is based on a progressive removal of water from the bioprosthetic tissue obtained with Polyethylene Glycol (e.g. MW 100 to 800) in aqueous solution ranging from 80% to 90%. The treatment is performed at a temperature between 20° C. to 50° C. for 12 h to 48 h. In order to obtain a more effective dehydration short chain alcohols can be added at a concentration of 10% to 20%.

The dehydration process is completed with a tissue drying for several hours in a clean environment. It allows a final storage of the bioprostheses in a dry packaging that is submitted to sterilization by means of Ethylene Oxide.

All the treatment processes, above described, can be performed on semi-finished assemblies or directly on the final assembled bioprostheses. In this case the processes can be applied as an individual prosthetic treatment.

BIBLIOGRAPHY

1. Schoen F J, Levy R J. Calcification of tissue heart valve substitutes: progress toward understanding and prevention. Ann Thorac Surg 2005; 79:1072-80.
2. Konakci K Z, Bohle B, Blumer R, Hoetzenecker W, Roth G, Moser B, Boltz-Nitulescu G, Gorlitzer M, Klepetko W, Wolner E, Ankersmit H J. Alpha-GAL on bioprostheses: xenograft immune response in cardiac surgery. Eur J Clin Invest 2005; 35:17-23.
3. Manji R A, Zhu L F, Nijjar N K, Rayner D C, Korbutt G S, Churchill T A, Rajotte R V, Koshal A, Ross D B. Glutaraldehyde-fixed bioprosthetic heart valve conduits calcify and fail from xenograft rejection. Circulation 2006; 114:318-27.
4. Vyavahare N, Hirsch D, Lerner E, Baskin J Z, Schoen F J, Bianco R, Kruth H S, Zand R, Levy R J. Prevention of bioprosthetic heart valve calcification by ethanol preincubation. Efficacy and mechanisms. Circulation 1997; 95:479-88.
5. Jorge-Herrero E, Ferna'ndez P, Escudero C, Garci'a-Pa'ez J M, Castilo-Olivares J L. Calcification of pericardial tissue pretreated with different amino acids. Biomaterials 1996; 17:571-5.
6. Bina Gidwani, Amber Vyas. A comprehensive review on cyclodextrin-based carriers for celivery of chemotherapeutic cytotoxic anticancer drugs. BioMed Research International Volume 2015, Article ID 198268, 15 pages http://dx.doi.org/10.1155/2015/198268.
7. Ankitkumar S. Jain, Abhijit A. Date, Raghuvir R. S. Pissurlenkar, Evans C. Coutinho, Mangal S. Nagarsenker. Sulfobutyl Ether$_7$ β-Cyclodextrin (SBE$_7$ β-CD) Carbamazepine complex: preparation, characterization, molecular modeling, and evaluation of in vivo anti-epileptic activity. AAPS PharmSciTech, Vol. 12, No. 4, December 2011; 1163-75.
8. E. M. Martin Del Valle. Cyclodextrins and their uses: a review. Process Biochemistry 39 (2004) 1033-1046.
9. Caroline Coisne, Sebastien Tilloy, Eric Monflier, Daniel Wils, Laurence Fenart, Fabien Gosselet. Cyclodextrins as emerging therapeutic tools in the treatment of cholesterol-associated vascular and neurodegenerative diseases. Molecules 2016, 21, 1748.
10. Narendra R. Vyavahare, Danielle Hirsch, Eyal Lerner, Jonathan Z. Baskin, Robert Zand, Frederick J.

Schoen, Robert J. Levy. Prevention of calcification of glutaraldehyde-crosslinked porcine aortic cusps by ethanol preincubation: Mechanistic studies of protein structure and water-biomaterial relationships. *J Biomed Mater Res,* 40, 577-585, 1998.
11. W. K. Ramp and D. N. Demaree, "Inhibition of net calcium efflux from bone by ethanol in vitro," *Am. J. Physiol.,* 246, C30-C36 (1984).
12. K. E. Friday and G. A. Howard, "Ethanol inhibits human bone cell proliferation and function in vitro," *Metabolism,* 40, 562-565 (1991).
13. E. Rubin and R. Hagai, "Ethanol-induced injury and adaptation in biological membranes," *Fed. Proc.,* 41, 2465-2471 (1982).
14. M. S. Tung and T. J. O'Farrell. The effect of ethanol on the solubility of dicalcium phosphate dihydrate in the system Ca(OH)2-H3PO4-H2O at 37° C. *J. Mol. Liq.,* 56, 237-243 (1993).
15. Narendra Vyavahare, Danielle Hirsch, Eyal Lerner, Jonathan Z. Baskin, Frederick J. Schoen, Richard Bianco, Howard S. Kruth, Robert Zand, Robert J. Levy. Prevention of bioprosthetic heart valve calcification by ethanol preincubation. Circulation. 1997; 95:479-488.
16. Anil Madhav Patwardhan, M.Ch., Pradeep Vaideeswar. Stress strain characteristics of glutaraldehyde treated porcine aortic valve tissue following ethanol treatment. *IJTCVS* 2004; 20: 67-71.

17. Vyavahare N R, Jones P L, Hirsch D, Levy R J. Prevention of glutaraldehyde-fixed bioprosthetic heart valve calcification by alcohol pretreatment: further mechanistic studies. J Heart Valve Dis. 2000 July; 9(4): 561-6.
18. Ming Shen, Ali Kara-Mostefa, Lin Chen, Michel Daudon, Marc Thevenin, Bernard Lacour, and Alain Carpentier. Effect of ethanol and ether in the prevention of calcification of bioprostheses. Ann Thorac Surg 2001; 71:5413-6.
19. Connolly J M, Alferiev I, Kronsteiner A, Lu Z, Levy R J. Ethanol inhibition of porcine bioprosthetic heart valve cusp calcification is enhanced by reduction with sodium borohydride. J Heart Valve Dis. 2004 May; 13(3):487-93.
20. Hyoung Woo Changa, Soo Hwan Kimb, Kyung-Hwan Kima, Yong Jin Kima. Combined anti-calcification treatment of bovine pericardium with amino compounds and solvents. Interactive CardioVascular and Thoracic Surgery 12 (2011) 903-907.
21. Kwan-Chang Kim, Soo-Hwan Kim, Yong-Jin Kim. Detoxification of glutaraldehyde treated porcine pericardium using L-Arginine & NABH$_4$. Korean J Thorac Cardiovasc Surg 2011; 44:99-107.
22. Evandro Antonio Sardeto, Francisco Diniz Affonso da Costa, Iseu do Santo Elias Affonso da COSTA, João Gabriel Roderjan, Eduardo Discher, Ricardo Alexandre Schneider, Carlos Henrique Gori Gomes, Claudinei Colattusso, Daniel Precoma, Andrea Dumsch, Sergio Veiga Lopes, Jairo Leal. Efficacy of AlCl$_3$ and ethanol in the prevention of calcification of fragments of porcine aortic wall fixed in GDA.

The invention claimed is:

1. A method of treating bioprosthetic tissues used for cardiovascular prostheses, the method comprising the step of:
   removing phospholipids from the bioprosthetic tissues by using a Cyclodextrin that is able by itself to remove phospholipids from the bioprosthetic tissues wherein the Cyclodextrin is a β-Cyclodextrin.

2. The method according to claim 1, wherein the bioprosthetic tissue is further treated with Polyethylene Glycol for achieving a tissue dehydration and with Ethylene Oxide for a sterilization of the bioprosthetic tissues.

3. The method according to claim 1, wherein the Cyclodextrin includes an element selected from the group consisting of: 2-hydroxypropyl β-Cyclodextrin, Sulfobutyl Ether β-Cyclodextrin, and Maltosyl β-Cyclodextrin.

4. The method according to claim 1, wherein the bioprosthetic tissues are further treated with Ethanol for removing phospholipids from the bioprosthetic tissues.

5. The method according to claim 4, wherein the bioprosthetic tissue is treated with Ethanol and Cyclodextrin simultaneously.

6. The method according to claim 4, wherein the bioprosthetic tissue is treated with Ethanol followed by the treatment with Cyclodextrin.

7. The method according to claim 4, wherein, the bioprosthetic tissue is treated with Cyclodextrin followed by the treatment with Ethanol.

8. The method according to claim 1, further comprising a step of cross-linking the bioprosthetic tissue.

9. The method according to claim 8, wherein the step of cross-linking occurs after removing phospholipids from the bioprosthetic tissue by using Cyclodextrin.

10. The method according to claim 8, further comprising a second treating of the bioprosthetic tissue with the Cyclodextrin, said second treating with Cyclodextrin being performed after the step of cross-linking.

11. The method according to claim 8, wherein the step of cross-linking occurs before the step of removing phospholipids from the bioprosthetic tissue by using Cyclodextrin.

* * * * *